United States Patent [19]

Guggenheim et al.

[11] Patent Number: 4,950,727

[45] Date of Patent: Aug. 21, 1990

[54] SPIRO(BIS)INDANE POLYAMIDE AND POLYIMIDE COPOLYSILOXANES AND METHOD OF PREPARATION

[75] Inventors: Thomas L. Guggenheim, Scotia; James A. Cella, Clifton Park; Sharon J. McCormick, Schenectady; Alice M. Colley, Latham; Jonathan D. Rich, Rexford; Philip J. McDermott, Clifton Park, all of N.Y.

[73] Assignee: General Electric Company, Schenectady, N.Y.

[21] Appl. No.: 182,020

[22] Filed: Apr. 15, 1988

Related U.S. Application Data

[63] Continuation-in-part of Ser. No. 146,154, Jan. 20, 1988, and a continuation-in-part of Ser. No. 157,009, Feb. 18, 1988, Pat. No. 4,814,496.

[51] Int. Cl.$^5$ .............................................. C08G 77/26
[52] U.S. Cl. ....................................... 528/26; 528/27; 528/28; 528/29
[58] Field of Search ............... 528/185, 352, 190, 195, 528/298, 26, 28, 29, 27

[56] References Cited

U.S. PATENT DOCUMENTS

| | | | |
|---|---|---|---|
| 3,856,752 | 12/1974 | Bateman et al. | 528/353 |
| 4,734,482 | 3/1988 | Tamai et al. | 528/185 |
| 4,736,016 | 4/1988 | Brunelle et al. | 528/370 |
| 4,757,132 | 7/1988 | Brunelle et al. | 528/357 |
| 4,789,725 | 12/1988 | Guggenheim et al. | 528/201 |
| 4,795,680 | 1/1989 | Rich et al. | 528/26 |
| 4,808,754 | 2/1989 | Guggenheim et al. | 528/335 |
| 4,814,496 | 3/1989 | Guggenheim | 562/466 |
| 4,826,916 | 5/1989 | Policastro et al. | 528/26 |
| 4,837,298 | 6/1989 | Cella et al. | 528/352 |
| 4,864,034 | 9/1989 | Cella et al. | 548/473 |
| 4,895,919 | 1/1990 | Faler et al. | 528/26 |

*Primary Examiner*—Veronica P. Hoke
*Attorney, Agent, or Firm*—William H. Pittman; James C. Davis, Jr.

[57] ABSTRACT

Linear polyamide and polyimide copolysiloxane compositions are prepared by contacting a strongly acidic catalyst, basic catalyst or alkali metal fluoride with a macrocyclic spirobiindane polyamide or polyimide disiloxane, either alone or in combination with a cyclic polysiloxane such as octamethylcyclotetrasiloxane.

20 Claims, No Drawings

SPIRO(BIS)INDANE POLYAMIDE AND POLYIMIDE COPOLYSILOXANES AND METHOD OF PREPARATION

This application is a continuation-in-part of copending applications Ser. No. 146,154, filed Jan. 20, 1988, and Ser. No. 157,009, filed Feb. 18, 1988, now U.S. Pat. No. 4,814,496.

This invention relates to linear copolysiloxanes, and more particularly to copolysiloxanes containing spiro(bis)indane moieties.

Various copolysiloxanes, especially those containing amide and imide moieties, are noteworthy because of their advantageous combinations of properties. They have potential for formulation to provide elastomeric and/or adhesive properties in combination with high solvent resistance and thermal stability. Therefore, there is continuing interest in copolysiloxanes of these types and methods for their preparation.

The present invention provides a class of copolysiloxane polyamides and polyimides containing spiro(bis)indane moieties. Also provided is a novel method for preparation of such copolysiloxanes from compositions comprising macrocyclic monomers and oligomers.

In one of its aspects, the invention includes linear polyamide and polyimide copolysiloxane compositions comprising spiro(bis)indane moiety-containing amide or imide units and polydiorganosiloxane units.

An essential feature of the compositions of this invention is the presence of spiro(bis)indane units of the formula

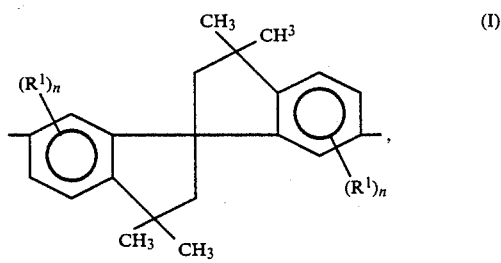

wherein each $R^1$ is independently $C_{1-4}$ primary or secondary alkyl or halo and n is 0–3. Such units are derived from the corresponding 6,6'-difunctional spiro(bis)indanes, especially those wherein n is 0 (hereinafter sometimes simply designated "spirobiindanes"). Such spirobiindane moieties may be derived from spirobiindane dicarboxylic or tetracarboxylic acids or spirobiindane diamines. Also present in said compositions are polydiorganosiloxane units.

Illustrative of the compositions of this invention are those comprising structural units of the formulas

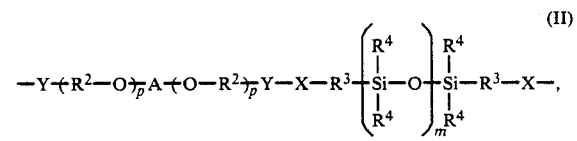

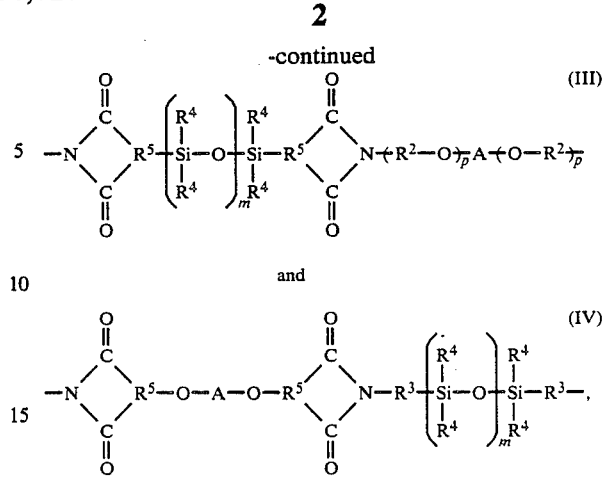

wherein:

A has formula I;

each of $R^2$ and $R^3$ is substituted or unsubstituted $C_{2-4}$ alkylene, m-phenylene or p-phenylene;

$R^4$ is $C_{1-4}$ primary or secondary alkyl, phenyl or substituted phenyl;

$R^5$ is a trivalent $C_{3-10}$ aliphatic or aromatic radical;

X is C(O) and Y is NH, or X is NH and Y is C(O);

m is from 1 to about 500; and p is 0 or 1.

In the compositions of formulas II, III and IV, the $R^2$ radicals are most often unsubstituted m- or p-phenylene. The value of p may be 0 or 1; that is, the $-O-R^2-$ moiety may be present or absent. The $R^3$ radicals may be alkylene or arylene as defined, with alkylene radicals most often being trimethylene. The $R^4$ values may be alkyl as defined, phenyl or substituted phenyl and are most often methyl.

In formula II, X may be C(O) and Y may be NH, or the reverse. In other words, it is not critical whether the spirobiindane moiety is derived from a dicarboxylic acid or a diamine, and the same is true of the polydiorganosiloxane moiety.

In formulas III and IV, the $R^5$ radicals are trivalent aliphatic or aromatic radicals, with aromatic radicals and especially those derived from benzene being preferred. Especially preferred are radicals of the formula

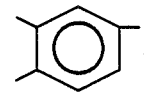

The compositions of this invention may be prepared by contacting a corresponding macrocyclic spirobiindane polyamide or polyimide disiloxane with a strongly acidic catalyst, a basic catalyst or an alkali metal fluoride. This method of preparation is another aspect of the invention.

Macrocyclic spirobiindane polyamides and polyimides containing disiloxane groups may be prepared as described in the aforementioned copending application Ser. No. 146,154, the disclosure of which is incorporated by reference herein. The identities of macrocyclic compositions corresponding to the compositions of this invention will be apparent to those skilled in the art. For example, typical macrocyclic compositions corresponding to formulas II, III and IV have the following formulas, respectively:

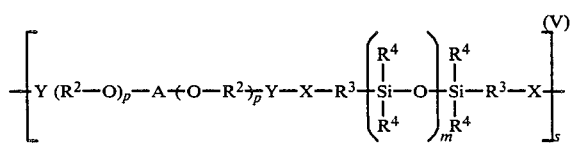

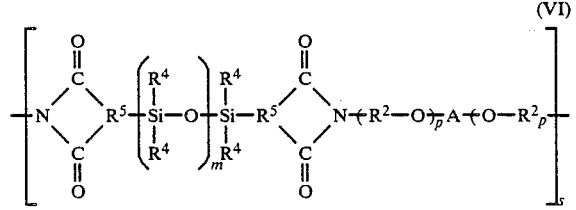

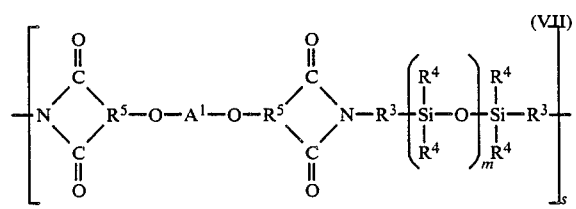

wherein s is from 1 to about 4.

Macrocyclic polyamides may be prepared from the corresponding diamines and dicarboxylic acid chlorides. The diamines in which $R^2$ is m- or p-phenylene and p is 1, and corresponding nitro compounds, are disclosed and claimed in copending, commonly owned application Ser. No. 20,264, filed Feb. 27, 1987 now U.S. Pat. No. 4,808,754.

The nitro compounds (herein after sometimes "bisnitrophenoxy ethers") may be prepared by the reaction of halonitrobenzenes or dinitrobenzenes with spirobiindane bisphenol salts under alkaline conditions in a dipolar aprotic solvent. The molar ratio of nitro compound to spirobiindane bisphenol salt is generally about 2.0–2.5:1. The corresponding bis-aminophenoxy ethers may be prepared by reduction of said bis-nitrophenoxy ethers by conventional means such as catalytic hydrogenation.

The preparation of the bis-nitrophenoxy and bis-aminophenoxy ethers is illustrated by the following examples. The compound 6,6'-dihydroxy-3,3,3'-3'-tetramethylspiro(bis)indane is designated "SBI" in the examples.

EXAMPLE 1

A reaction vessel fitted with a mechanical stirrer, reflux condenser and nitrogen purge means was charged with 45.9 grams (149 mmol.) of SBI, 49.31 grams (313 mmol.) of p-chloronitrobenzene, 61.68 grams (447 mmol.) of potassium carbonate and 700 ml. of dry dimethylformamide. The mixture was purged with nitrogen and heated at 150° C. with stirring for 14 hours. It was then poured into 1.5 liters of ice water with rapid stirring, and the precipitated 6,6'-bis(4-nitrophenoxy)-3,3,3',3'-tetramethyl--1,1'-spiro(bis)indane was recrystallized from methyl ethyl ketone. The yield was 73.7 grams (90% of theoretical) of a crystalline product, m.p. 200.5°–201.5° C. The structure was confirmed by elemental analysis.

EXAMPLE 2

A mixture of 5.27 grams (9.58 mmol.) of the product of Example 1, 100 mg. of platinum oxide and 100 ml. of tetrahydrofuran was pressurized with hydrogen at 50 psi. and shaken for 3 hours at room temperature. The mixture was filtered, using a filter aid material, and the filtration residue was washed with methylene chloride. The combined filtrates were vacuum stripped to yield 4.6 grams (98% of theoretical) of 6,6'-(4-aminophenoxy)-3,3,3',3'-tetramethyl-1,1'-spiro(bis)indane, which was recrystallized from toluene to yield the pure product as fine crystals, m.p. 214°–215° C. The structure was confirmed by elemental analysis.

EXAMPLE 3

In a reaction vessel similar to that of Example 1, a mixture of 24.51 grams (79.6 mmol.) of SBI, 27.40 grams (163.1 mmol.) of m-dinitrobenzene, 43.93 grams (318.4 mmol.) of potassium carbonate and 175 ml. of dimethyl sulfoxide was heated for 30 hours at 140° C., under nitrogen. The mixture was cooled and diluted with 500 ml. of methylene chloride, and was washed with 10% aqueous sodium hydroxide solution, water and aqueous sodium chloride solution. The organic phase was filtered and the filtration residue was rinsed with methylene chloride. The combined filtrates were vacuum stripped to yield 42.5 grams of the product as a thick oil. A portion of the oil was purified by medium pressure liquid chromatography of an ethyl acetate-hexane solution over silica gel. The purified 6,6'-(3-nitrophenoxy)-3,3,3',3'-tetramethyl-1,1'-spiro(bis)indane was obtained in 66% yield, m.p. 174°–175° C. The structure was confirmed by elemental analysis.

EXAMPLE 4

Following the procedure of Example 2, 2.5 grams (4.5 mmol.) of the product of Example 3 was hydrogenated over a platinum oxide catalyst. Upon solvent removal and recrystallization from a toluene-cyclohexane mixture, there was obtained 1.8 grams (80% of theoretical) of analytically pure 6,6'-(3-aminophenoxy)-3,3,3',3'-tetramethyl-1,1'-spiro(bis)indane, m.p. 190°–197° C. with decomposition. The structure was confirmed by elemental analysis.

Also useful for the preparation of macrocyclic polyamide disiloxanes are spiro(bis)indane bis(carboxyphenyl ethers) of the formula

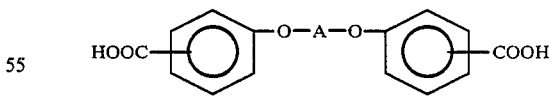

and their functional derivatives. They are disclosed and claimed in the aforementioned copending, commonly owned application Ser. No. 157,009 now U.S. Pat. No. 4,814,496.

Ester derivatives of said bis(carboxyphenyl ethers) be prepared by the nucleophilic displacement reaction of a di-(alkali metal) salt of the spirobiindane bisphenol with a nuclear nitro- or halo-substituted benzoic acid ester, typically a lower alkyl ester and preferably the methyl or ethyl ester. Suitable compounds include ethyl p-nitrobenzoate, ethyl m-nitrobenzoate, methyl p- chlorobenzoate and methyl m-bromobenzoate. The nitro compounds are frequently preferred. The nucleophilic displacement reaction is typically conducted at a temperature of about 80°–125° C. in a dipolar aprotic solvent such as dimethylformamide, dimethylacetamide, dimethyl sulfoxide or N-methylpyrrolidone.

Upon saponification under conventional conditions of the esters thus prepared, the salts of the bis-carboxyphenyl ethers are obtained. The salts may be converted to the free acids, which may in turn be converted to the acyl halides by reaction with such conventional intermediates as phosphorus trichloride, phosphorus pentachloride or thionyl chloride. phosphorus trichloride, phosphorus pentachloride or thionyl chloride.

The preparation of the bis(carboxyphenyl ethers) is illustrated by the following example.

EXAMPLE 5

Freshly cut sodium metal, 14.26 grams (620 mmol.), was added carefully, with stirring, to 1 liter of anhydrous methanol in a nitrogen atmosphere over 2 hours. To the resulting sodium methoxide solution was added, with stirring, 95 grams (310 mmol.) of SBI. Stirring was continued until the mixture was homogeneous after which the methanol was removed under reduced pressure. The resulting SBI disodium salt was washed with two 500-ml. portions of toluene and vacuum stripped, and was finally dried by heating to 100° C. for 12 hours under vacuum.

A mixture of 3.52 grams (10 mmol.) of the SBI disodium salt, 3.93 grams (20 mmol.) of ethyl p-nitrobenzoate and 50 ml. of dry dimethylformamide was heated at 100° C. in a nitrogen atmosphere until homogeneity was achieved. Chloroform, 200 ml. was added and the mixture was extracted three times with aqueous hydrochloric acid solution and once with aqueous sodium chloride solution. The organic phase was dried over anhydrous magnesium sulfate, filtered and vacuum stripped. The residual oil was diluted with methanol and stirred, whereupon a tan solid precipitated which was collected by filtration, washed with methanol and recrystallized from 100% ethanol. There was obtained 4.93 grams (82% of theoretical) of the desired SBI bis(p-carboxyphenyl ether) ethyl ester, melting at 106°–108° C. Its identity was confirmed by infrared, proton nuclear magnetic resonance and mass spectroscopy and elemental analysis.

A mixture of 67.54 grams (112 mmol.) of the SBI bis(p-carboxyphenyl ether) ethyl ester, 25.05 grams (447 mmol.) of potassium hydroxide and 500 ml. of ethylene glycol was heated at 120° C., with stirring, until it became homogeneous. The mixture was then poured into aqueous hydrochloric acid solution and the resulting precipitate was collected by filtration, washed with water and air dried. The product, the desired SBI bis(p-carboxyphenyl ether), was obtained in 99% yield and had a melting point of 318°–321° C. Its identity was confirmed by carbon-13 nuclear magnetic resonance and mass spectroscopy.

A mixture of 60 grams (110 mmol.) of the SBI bis(p-carboxyphenyl ether) and 750 ml. of thionyl chloride was heated under reflux in a nitrogen atmosphere for 3 ½ hours, with stirring, whereupon it became homogeneous. The mixture was distilled with the removal of 700 ml. of liquid at atmospheric pressure, and was then diluted with 400 ml. of toluene. Distillation was resumed to remove 350 ml. of liquid, after which toluene addition and distillation were repeated. The residue was cooled and recrystallized from a mixture of hexane and toluene to yield the desired bis(carboxy ether) chloride, melting at 161°–163° C., in 96% yield. Its identity was confirmed by infrared, carbon-13 nuclear magnetic resonance and mass spectroscopy and elemental analysis.

The macrocyclic polyimides may be prepared by reacting an appropriate diamine with an appropriate tetracarboxylic acid or functional derivative thereof. Suitable functional derivatives include dianhydrides and bisimides containing electron-deficient N-substituents; the latter are disclosed in U.S. Pat. No. 4,578,470, the disclosure of which is incorporated by reference herein. The dianhydrides are preferred. Frequent reference to said dianhydrides will be made hereinafter, but it should be understood that the free acids and other appropriate functional derivatives may be substituted therefor.

For the most part, approximately equimolar proportions of diamine and dianhydride are heated at a temperature in the range of about 120°–250° C., with water of reaction being removed by distillation. It is frequently preferred to employ a relatively high boiling organic solvent, typically a chlorinated aromatic hydrocarbon such as o-dichlorobenzene or a dipolar aprotic solvent such as dimethyl sulfoxide or dimethylacetamide. The presence of a metal carboxylate or oxygenated phosphorus compound as a catalyst, in accordance with U.S. Pat. Nos. 4,293,683 and 4,324,882, is also often beneficial. The disclosures of these patents are also incorporated by reference herein.

Tetracarboxylic acids of the formula

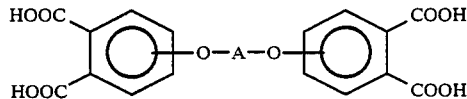

and their functional derivatives are novel compounds and are disclosed and claimed in copending, commonly owned application Ser. No. 146,155, filed Jan. 20, 1988 now U.S. Pat. No. 4,864,034. The bisimides may be prepared by the reaction of the corresponding spirobiindane bisphenols with nitro-N-alkylphthalimides and converted to dianhydrides by methods similar to those employed to prepare the corresponding bisphenol A reaction products. The following example is illustrative.

EXAMPLE 6

SBI, 15.4 grams (50 mmol.), was added portionwise to a slurry of 262 grams (102 mmol.) of sodium hydride in 100 ml. of dry dimethylformamide. The mixture was heated for one hour at 75° C. in a nitrogen atmosphere, after which 20.6 grams (100 mmol.) of 4-nitro-N-methylphthalimide was added. The resulting mixture was heated for 1 ½ hours at 110° C., cooled and poured into 3 volumes of cold water. The solid which precipitated was filtered and suspended in a mixture of toluene and 2% aqueous sodium hydroxide solution and the mixture was cooled and filtered; the organic phase of the filtrate was dried and vacuum stripped. The combined solids were the desired 6,6'-bis(3,4-dicarboxyphenoxy)-3,3,3',3'-tetramethylspiro(bis)indane bis-N-methylimide (27.07 grams, 86.5% of theoretical). Its melting point after recrystallization from toluene was 217.5°–218° C. The structure was confirmed by proton nuclear magnetic resonance and field desorption mass spectrometry.

A solution of 14 grams (22.36 mmol.) of the bisimide in 16.7 grams of a 45% aqueous potassium hydroxide solution and 20 ml. of water was heated under reflux, with water and methylamine being removed by distillation and water being replenished. Heating was continued for 4 days, until the distillate was neutral to pH paper. The solution was cooled and added slowly to cold concentrated hydrochloric acid, and the tetracarboxylic acid which precipitated was collected by filtration, dried and dissolved in a mixture of 25 ml. of chlorobenzene and 5 ml. of acetic anhydride. Upon heating under reflux for 2 ½ hours and cooling, the desired dianhydride (10.3 grams, 77% of theoretical) precipitated and was filtered and dried; it melted at 233°–234° C. The structure was confirmed spectroscopically as for the bisimide.

The preparation of macrocyclic polyamide and polyimide diorganosiloxane compositions is illustrated by the following examples.

EXAMPLE 7

A solution of 7 grams (11.97 mmol.) of SBI bis(p-carboxyphenyl ether) chloride and 229 ml. of dry, ethanol-free chloroform was heated under reflux in a nitrogen atmosphere, with stirring, and a mixture of 3.78 grams (11.97 mmol.) of 1,3-bis(m-aminophenyl)tetramethyldisiloxane, 1.89 grams (23.92 mmol.) of pyridine and 10 ml. of dry chloroform was added over 1 hour. The mixture was washed twice with aqueous hydrochloric acid solution and once with aqueous sodium chloride solution, dried over magnesium sulfate and filtered. The filtrate was vacuum stripped to yield an off-white solid in 98% yield. Analysis of the solid by high pressure liquid chromatography and field desorption mass spectrometry showed the presence of 94% macrocyclic polyamide oligomers, including the monomeric and dimeric species, and 6% linear polyamide.

EXAMPLE 8

A solution of 1.274 grams (5 mmol.) of 1,9-diamino-4,4,6,6-tetramethyl-4,6-disila-5-oxanonane in 50 ml. of o-dichlorobenzene was added over 1 hour to a solution of 3 grams (5 mmol.) of the dianhydride of Example 6 and 2 mg. of sodium phenylphosphonate in 250 ml. of o-dichlorobenzene, at 140° C. When the addition was completed, the temperature was raised to 225° C. and o-dichlorobenzene and water were removed by distillation until the distillate was no longer cloudy; a total of about 100 ml. of o-dichlorobenzene was thus removed. The residual solution was heated under reflux for 2 hours and then reduced to about 10% of its original volume by distillation. Upon cooling and pouring into 5 volumes of methanol, a solid precipitated which was collected by filtration and dried in a vacuum oven at 110° C. It was shown by field desorption mass spectrometry to comprise the desired macrocyclic siloxane polyetherimide monomer and dimer. A further portion of macrocyclic monomer was obtained by evaporation of the methanol from the filtrate. The total yield of macrocyclic oligomers was 3.34 grams, or 82% of theoretical.

EXAMPLE 9

The procedure of Example 8 was repeated, replacing the diamine on an equimolar basis with bis(3-aminophenyl)tetramethyldisiloxane. There was obtained 3.87 grams (85% of theoretical) of a white solid comprising a mixture of linear siloxane polyetherimide and macrocyclic oligomers.

EXAMPLE 10

A solution of 11 grams (22 mmol.) of the diamine of Example 2 and 10 mg. of sodium pyrophosphate in 1000 ml. of o-dichlorobenzene was heated under reflux, with stirring, and a solution of 9.42 grams (22 mmol.) of 1,3-bis(3,4-dicarboxyphenyl)tetramethyldisiloxane dianhydride in 120 ml. of o-dichlorobenzene was added over ½ hour. The mixture was heated under reflux for 2 hours, after which about 200 ml. of solvent was removed by distillation and refluxing was continued for another 3 hours. The solution was concentrated by distillation to about 200 ml., cooled and added to 1 liter of hexane, with stirring. A solid product precipitated and was collected by filtration and air-dried. The yield was 18.5 grams, or 94% of theoretical. It was shown by high pressure liquid chromatography and field desorption mass spectrometry to include 90% macrocyclic siloxane polyetherimide oligomers having degrees of polymerization from 1 to 5, and 10% linear siloxane polyetherimide. Upon recrystallization from o-dichlorobenzene, there was obtained substantially pure macrocyclic monomer melting at 295°–299° C.

The catalysts useful in the method of this invention are strongly acidic catalysts such as methanesulfonic and trifluoromethanesulfonic acid, basic catalysts such as alkali metal phenates, and alkali metal fluorides. Among the latter, cesium fluoride is frequently preferred because of its high solubility in the macrocyclic compositions.

When only the macrocyclic composition (e.g., of formula V, VI or VII) and catalyst are present, the product is one in which m is 1. It is also possible to incorporate in the polymerization mixture a cyclic polysiloxane such as octamethylcyclotetrasiloxane, to increase the value of m to a maximum level of about 500.

The proportion of catalyst in the mixture, based on macrocyclic composition and cyclic polysiloxane present, may vary widely and is typically about 0.001–10.0 mole percent. Polymerization temperatures are typically in the range of about 125°–200° C. It may sometimes be advantageous to employ a non-polar solvent such as o-dichlorobenzene or 1,2,4-trichlorobenzene as a reaction medium.

The present invention is illustrated by the following examples.

EXAMPLE 11

A mixture of 250 mg. of the product of Example 7, 1 gram (3.38 mmol.) of octamethylcyclotetrasiloxane, 5 microliters (0.08 mmol.) of methanesulfonic acid and 2 ml. of dry chloroform was heated at 70° under nitrogen, with stirring, to remove the chloroform. There remained a thick polymeric residue which was shown by gel permeation chromatography to have a weight average molecular weight of about 78,000.

EXAMPLE 12

A solution of 26.7 mg. of the macrocyclic siloxane polyetherimide monomer product of Example 8 and 1 microliter of methanesulfonic acid in 100 microliters of 1,2,4-trichlorobenzene was heated at 140° C. for one hour, with periodic analysis by gel permeation chromatography. After 40 minutes, the weight average molecular weight relative to polystyrene was about 20,000 and no further increase was noted.

The solution was poured onto a glass plate and allowed to thicken overnight. It was then heated in a vacuum oven for 2 hours at 140° C., yielding a clear, colorless film with excellent integrity. The film had a weight average molecular weight of about 200,000 and a glass transition temperature of 109° C.

EXAMPLE 13

A mixture of 25 mg. of the macrocyclic siloxane polyetherimide monomer product of Example 8 and 1 microliter of methanesulfonic acid was heated for 10 minutes at 250° C., after which gel permeation chromatographic analysis showed a weight average molecular weight relative to polystyrene of 26,200. The product was cooled, dissolved in chloroform and cast on a glass slide which was then heated for 1 hour at 140° C., to produce a polymer film with a molecular weight of 39,800.

EXAMPLE 14

A solution of 600 mg. (0.68 mmol.) of the macrocyclic siloxane polyetherimide of Example 10 and 8 mg. (0.06 mmol.) of sodium p-cresoxide in 1.8 ml. of o-dichlorobenzene was heated under reflux in a nitrogen atmosphere for 4 hours, with stirring. The solution was cooled and poured slowly into 50 ml. of hexane, with stirring, and the solid polymer which precipitated was filtered and dried. It had a weight average molecular weight relative to polystyrene of 15,000.

EXAMPLE 15

A solution of 130 mg. (0.15 mmol.) of the macrocyclic siloxane polyetherimide of Example 10, 220 mg. (0.74 mmol.) of octamethylcyclotetrasiloxane and 2 microliters (0.02 mmol.) of trifluoromethanesulfonic acid in 1.5 ml. of freshly distilled chloroform was heated under nitrogen for 12 hours at 60° C., with stirring. Upon analysis by gel permeation chromatography, the product was found to comprise 80% by weight of a polyetherimide polysiloxane having a weight average molecular weight of 8,000.

What is claimed is:

1. A linear polyamide or polyimide copolysiloxane composition comprising spiro(bis)indane moiety-containing amide or imide units and polydiorganosiloxane units.

2. A composition according to claim 1 comprising structural units of one of the formulas

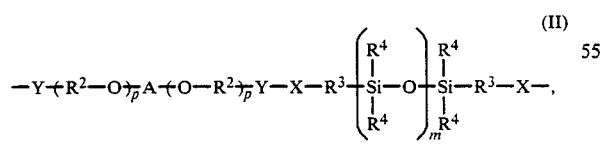

(II)

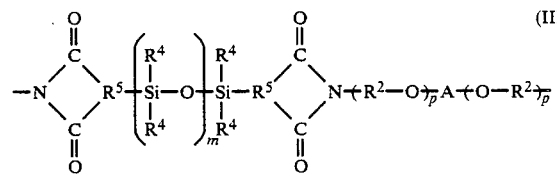

(III)

and

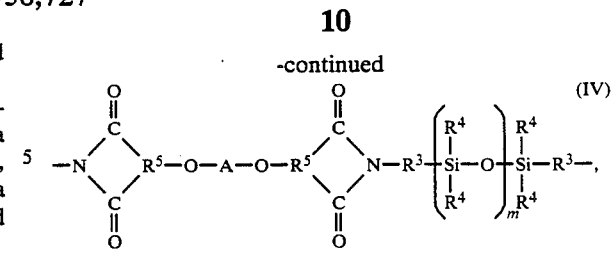

(IV)

wherein:

A is a spiro(bis)indane moiety of the formula

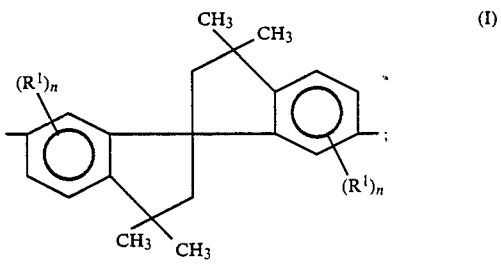

(I)

each $R^1$ is independently $C_{1-4}$ primary or secondary alkyl or halo;

each of $R^2$ and $R^3$ is substituted or unsubstituted $C_{2-4}$ alkylene, m-phenylene or p-phenylene;

$R^4$ is $C_{1-4}$ primary or secondary alkyl, phenyl or substituted phenyl;

$R^5$ is a trivalent $C_{3-10}$ aliphatic or aromatic radical;

X is C(O) and $Y^1$ is NH, or X is NH and Y is C(O);

m is from 1 to about 500;

n is 0–3; and p is 0 or 1.

3. A composition according to claim 2 wherein n is 0 and $R^4$ is methyl.

4. A composition according to claim 3 which is a polyamide comprising structural units of formula II.

5. A composition according to claim 4 wherein p is 1 and $R^2$ is p-phenylene.

6. A composition according to claim 5 wherein X is NH and Y is C(O).

7. A composition according to claim 6 wherein $R^3$ is p-phenylene.

8. A composition according to claim 3 which is a polyimide comprising structural units of formula III.

9. A composition according to claim 8 wherein $R^5$ is

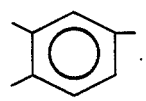

10. A composition according to claim 9 wherein p is 1.

11. A composition according to claim 10 wherein $R^2$ is p-phenylene.

12. A composition according to claim 3 which is a polyimide comprising structural units of formula IV.

13. A composition according to claim 12 wherein $R^5$ is

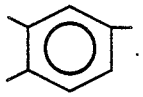

14. A composition according to claim 13 wherein $R^3$ is trimethylene.

15. A composition according to claim 13 wherein $R^3$ is m-phenylene.

16. A method for preparing a composition according to claim 1 which comprises contacting a corresponding macrocyclic spirobiindane polyamide or polyimide disiloxane with a strongly acidic catalyst, a basic catalyst or an alkali metal fluoride.

17. A method according to claim 16 wherein the catalyst is methanesulfonic or trifluoromethanesulfonic acid, an alkali metal phenate or cesium fluoride.

18. A method according to claim 17 wherein the reaction mixture also contains a cyclic polysiloxane.

19. A method according to claim 18 wherein the cyclic polysiloxane is octamethylcyclotetrasiloxane.

20. A method according to claim 17 wherein the polymerization temperature is in the range of about 125°–200° C.

* * * * *